US008258325B2

(12) United States Patent
Grass et al.

(10) Patent No.: US 8,258,325 B2
(45) Date of Patent: Sep. 4, 2012

(54) MIXTURE OF DIESTERS OF DIANHYDROHEXITOL DERIVATIVES WITH CARBOXYLIC ACIDS OF THE EMPIRICAL FORMULA $C_8H_{17}COOH$, PROCESS FOR PREPARING THESE DIESTERS, AND USE OF THESE MIXTURES

(75) Inventors: Michael Grass, Haltern am See (DE); Norbert Scholz, Recklinghausen (DE); Alfred Kaizik, Marl (DE); Wilfried Bueschken, Haltern am See (DE); Hans-Gerd Lueken, Marl (DE)

(73) Assignee: Evonik Oxeno GmbH, Marl (DE)

( * ) Notice: Subject to any disclaimer, the term of this patent is extended or adjusted under 35 U.S.C. 154(b) by 488 days.

(21) Appl. No.: 12/523,906

(22) PCT Filed: Dec. 21, 2007

(86) PCT No.: PCT/EP2007/064463
§ 371 (c)(1),
(2), (4) Date: Jul. 21, 2009

(87) PCT Pub. No.: WO2008/095571
PCT Pub. Date: Aug. 14, 2008

(65) Prior Publication Data
US 2009/0301348 A1 Dec. 10, 2009

(30) Foreign Application Priority Data
Feb. 5, 2007 (DE) .......................... 10 2007 006 442

(51) Int. Cl.
*C07D 307/93* (2006.01)
*C07D 493/00* (2006.01)
*C08G 73/06* (2006.01)
(52) U.S. Cl. .................. 549/464; 549/465; 528/424
(58) Field of Classification Search .................. 549/464, 549/465; 528/424
See application file for complete search history.

(56) References Cited

U.S. PATENT DOCUMENTS 6,395,810 B1 * 5/2002 Luitjes et al. ................. 524/109
6,693,209 B2 * 2/2004 Van Es et al. ................. 554/229

FOREIGN PATENT DOCUMENTS
JP 8188770 7/1996
WO 99 45060 9/1999
WO WO2008/156159 12/2008

OTHER PUBLICATIONS

Hachihama, Yoshikazu et al., "Studies on the Preparation of Plasticizers from Carbohydrate Sources, I. Levulinic Acid Esters, II. Sorbide Esters", Technology Reports of the Osaka University, vol. 3, No. 72, pp. 191-200, (1953).

* cited by examiner

*Primary Examiner* — Andrew D. Kosar
*Assistant Examiner* — Raymond Covington
(74) *Attorney, Agent, or Firm* — Oblon, Spivak, McClelland, Maier & Neustadt, L.L.P.

(57) ABSTRACT

The present invention relates to a mixture comprising diesters of the formula (I) where $R^1$ to $R^8$=H or alkyl group having from 1 to 6 carbon atoms, where the $R^1$ to $R^8$ radicals may be the same or different, which is characterized in that at least two different diesters I are present in the mixture, said diesters differing in the structure of at least one of the carboxylic acid radicals $C^8H^{17}COO$ present, to a process for preparing diesters of an isosorbide derivative of the formula I, in which a hexahydric alcohol and/or a monoanhydro or dianhydro derivative of the alcohol is esterified with a mixture of at least two different carboxylic acids of the empirical formula $C^8H^{17}COOH$, and to the use of these mixtures in paints, inks or coatings, in plastisols, adhesives or adhesive components, in sealants, as plasticizers in polymers or polymer components, as solvents, as lubricant oil components and as assistants in metal processing, and also PVC compositions or plastisols comprising PVC and from 5 to 250 parts by mass of the mixture per 100 parts by mass of PVC.

32 Claims, 1 Drawing Sheet

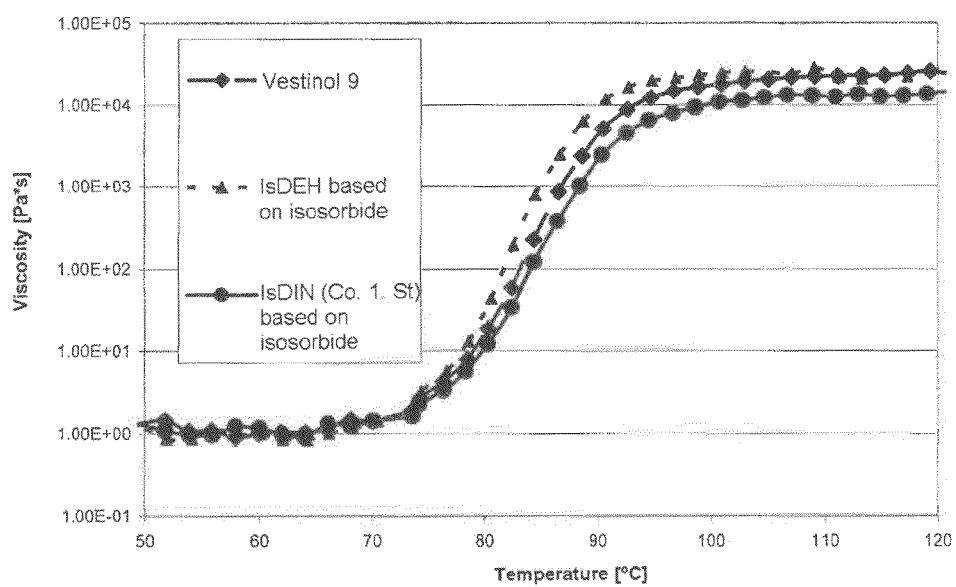

MIXTURE OF DIESTERS OF DIANHYDROHEXITOL DERIVATIVES WITH CARBOXYLIC ACIDS OF THE EMPIRICAL FORMULA C$_8$H$_{17}$COOH, PROCESS FOR PREPARING THESE DIESTERS, AND USE OF THESE MIXTURES

The present invention relates to a mixture of diesters of dianhydrohexitol derivatives with carboxylic acids of the empirical formula C$_8$H$_{17}$COOH, in particular of isosorbide esters of these carboxylic acids. The present invention likewise relates to a process for preparation of these esters or mixtures and to their use.

Polyvinyl chloride (PVC) is one of the most commercially important polymers. It is widely used both in the form of rigid PVC and in the form of flexible PVC.

To produce a flexible PVC, plasticizers are added to the PVC, and in most cases here phthalic esters are used, in particular di-2-ethylhexyl phthalate (DEHP), diisononyl phthalate (DINP) and diisodecyl phthalate (DIDP). Examples of other plasticizers used alongside these for plastics such as polyvinyl chloride (PVC), polyvinyl butyral (PVB) and polyolefins are alicyclic polycarboxylic esters, such as the esters of cyclohexane-1,2-dicarboxylic acid, since they are regarded as less hazardous in terms of risk to health than the corresponding phthalic esters. The abovementioned esters can moreover be used as a component of lubricating oil or as auxiliary in metalworking.

The abovementioned aromatic or aliphatic polycarboxylic esters are entirely based on fossil raw materials, which have only limited availability. In order to conserve fossil resources, there is therefore a need for polycarboxylic esters which are at least to some extent based on renewable raw materials.

WO 99/45060 discloses the use of isosorbide derivatives, and in particular of isosorbide esters, as plasticizers, e.g. for polyvinyl chloride (PVC). For preparation of the esters, isosorbide is reacted with the corresponding carboxylic acids. The carboxylic acid radicals can have from 3 to 12 carbon atoms, possible carboxylic acid radicals explicitly mentioned here being butanoyl, hexanoyl, 2-ethylhexanoyl, octanoyl and decanoyl. In the examples, preparation of isosorbide dioctanoate, isosorbide dibutanoate, isosorbide dihexanoate and isosorbide bis(2-ethylhexanoate) is described.

WO 01/83488 describes a process for preparation of isosorbide esters, in which dianhydroglycitol, monoanhydroglycitol or glycitol is reacted with the corresponding carboxylic acid, which preferably has from 3 to 20 carbon atoms, in the presence of a macroporous, acidic ion-exchanger resin. The molar ratio here of ((di)anhydro)glycitol to carboxylic acid is from 2 to 5. The description says that the reaction can be carried out with branched or unbranched acids. Examples mentioned of possible acids are propanoic acid, hexanoic acid, octanoic acid, nonanoic acid or decanoic acid. The examples react octanoic acid or 2-ethylhexanoic acid with isosorbide.

Starting from the known prior art, the object of the present invention was to provide alternative isosorbide esters which have good suitability as plasticizer in particular for plasticizing PVC.

When the two commercially available nonanoic acids, pelargonic acid (n-nonanoic acid) and 3,5,5-trimethyl-hexanoic acid, were used for preparation of the corresponding dianhydrohexitol derivatives, it was found that the resultant esters have only limited usefulness as plasticizers for PVC.

Surprisingly, however, it has been found that dianhydrohexitol diesters, in particular isosorbide diesters, of carboxylic acids having 9 carbon atoms which comprise a mixture of at least two structurally different nonanoic acids and preferably have a certain degree of branching have particularly good suitability as plasticizer, in particular as plasticizer for PVC.

The present invention therefore provides a mixture comprising diesters of the formula I of a dianhydro-hexitol derivative with carboxylic acids of the empirical formula C$_8$H$_{17}$COOH

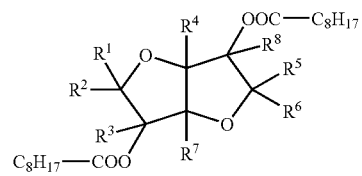

I where R$^1$ to R$^8$=H or alkyl group having from 1 to 6 carbon atoms, R$^1$ to R$^8$ being identical or different, characterized in that in the mixture at least two different diesters I are present which differ in the constitution of at least one of the carboxylic acid radicals C$_8$H$_{17}$COO present.

The present invention likewise provides a process for preparation of diesters of the formula I, characterized in that a hexahydric alcohol of the formula II

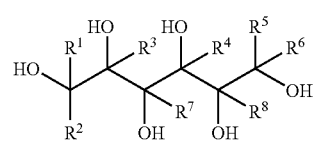

II where the radicals R$^1$ to R$^8$ are as defined in formula I, and/or an anhydro or dianhydro derivative of an alcohol of the formula II is reacted with a mixture which comprises at least two different carboxylic acids of the empirical formula C$_8$H$_{17}$COOH.

The present invention also provides the use of the inventive mixtures in a paint, in an ink or in a coating, in a plastisol, in an adhesive or in a component of an adhesive, in a sealing composition, as a plasticizer in a plastic or in a component of a plastic, as a solvent, as a component of a lubricating oil or as an auxiliary during metalworking, and a PVC composition or a plastisol, comprising PVC and from 5 to 250 parts by weight of the inventive mixture per 100 parts by weight of PVC.

An advantage of the inventive mixtures is that they are to some extent based on renewable raw materials, and availability, including future availability, has thus been ensured. Initial investigations have shown that dialkanoylisosorbide esters also generally have advantageous toxicological properties (van Haveren et al., ACS symposium series 2006, Vol 921, pages 99 to 115). Good biodegradability is moreover to be expected in cases where no, or only a small number of, quaternary carbon atoms are present in the acid radical.

In comparison with mixtures comprising compounds of the formula I which are based on only one carboxylic acid isomer or whose carboxylic acid radicals have a degree of branching smaller than 0.7, the inventive mixtures generally feature better miscibility with PVC. By way of example, the isosorbide diester of n-nonanoic acid (pelargonic acid) is solid at room temperature, and this makes any use in plastisol applications difficult or impossible. In comparison with mixtures comprising compounds of the formula I whose degree of branching of the carboxylic acid radicals is greater than 2.0, the inventive mixtures feature markedly improved low-temperature properties (flexibilization of the plastic at low temperatures) and lower viscosity in plastisols.

For the purposes of the present invention, isononanoic acid or isononanol always means an isomer or a mixture of isomers of nonanoic acid and, respectively, of nonanol. Isononanoic acid or isononanol can therefore comprise not only branched but also unbranched isomers.

A feature of the inventive mixtures comprising diesters of a dianhydrohexitol derivative with carboxylic acids of the empirical formula $C_8H_{17}COOH$ of the formula I

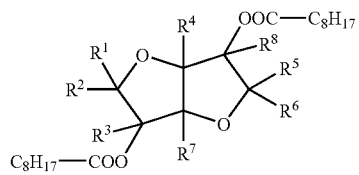

where $R^1$ to $R^8$=H or alkyl group having from 1 to 6 carbon atoms, $R^1$ to $R^8$ being identical or different, is that in the mixture at least two different diesters I are present which differ in the constitution of at least one and/or both of the carboxylic acid radicals $C_8H_{17}COO$ present. The mixtures here can comprise diesters in which one or both carboxylic acid radicals are unbranched, singly branched and/or multiply branched carboxylic acid radicals.

The composition of the inventive mixtures is preferably such that the carboxylic acids obtained via hydrolysis of the diester mixtures comprise at least two carboxylic acids of the empirical formula $C_8H_{17}COOH$ with a different constitutional formula, the proportion present of any of the carboxylic acids present in the mixture not being more than 95 mol %, preferably at least 90 mol %.

It can be advantageous if the carboxylic acids of the empirical formula $C_8H_{17}COOH$ obtained via hydrolysis of the diesters of the formula I present in the inventive mixture comprise less than 10 mol %, preferably less than 5 mol %, particularly preferably less than 1 mol % and very particularly preferably from 0.0001 to 1 mol %, of 3,5,5-trimethylhexanoic acid or of other triply substituted nonanoic acids, in particular those having quaternary carbon atoms.

It is preferable that mixtures of carboxylic acids of the empirical formula $C_8H_{17}COOH$ obtained via hydrolysis of the inventive mixtures of diesters of the formula I comprise less than 1 mol %, preferably less than 0.001 mol %, and with preference no, acids which have a quaternary carbon atom. An advantage of this is that the corresponding acids or esters are more biodegradable, their environmental balance therefore being better.

It can also be advantageous if the carboxylic acids of the empirical formula $C_8H_{17}COOH$ obtained via hydrolysis of the diesters of the formula I present in the inventive mixture comprise from 1 to 85%, in particular from 1 to 50%, preferably from 2 to 20%, of n-nonanoic acid.

The hydrolysis of the diesters of the formula I can take place by conventional methods via reaction with alkaline media (see, for example, Ullmann's Enzyklopädie der Technischen Chemie [Ullmann's Encyclopaedia of Industrial Chemistry], 5 Ed. A 10, pp. 254-260, 1986). A conventional method, e.g. gas-chromatographic analysis methods (GC), can be used to determine the proportions of the carboxylic acids in the mixture obtained, in particular the proportion of 3,5,5-trimethylhexanoic acid, preferably after derivatization to give the methyl ester or silyl ester.

The carboxylic acid radicals of the empirical formula $C_8H_{17}COO$ of the diesters present in the mixture particularly preferably have an average degree of branching of from 0.7 to 2.0, preferably from 0.9 to 1.9, with preference from 1.0 to 1.8 and with particular preference from 1.2 to 1.7. The carboxylic acid radicals here are those based on a mixture of two or more isomers of the carboxylic acid of the empirical formula $C_8H_{17}COOH$.

$^1$H NMR methods can be used to determine the average degree of branching when, as in the isosorbide diester of carboxylic acids of the empirical formula $C_8H_{17}COOH$, the diesters present are only those having no substitution on the ring. According to the present invention, the degree of branching is preferably determined with the aid of $^1$H NMR spectroscopy on a solution of the diesters in deuterochloroform ($CDCl_3$). By way of example, the spectra can be recorded by dissolving 20 mg of substance in 0.6 ml of $CDCl_3$ (comprising 1% by weight of TMS) and charging this solution to an NMR tube of diameter 5 mm. Both the substance to be studied and the $CDCl_3$ used can first be dried over molecular sieve, in order to exclude measurement of any false values due to any water present. The method of determining the degree of branching is advantageous in comparison with other methods for characterizing alcohol radicals as described by way of example in WO 03/029339, since water contamination has in essence no effect on results found and their evaluation. Since in the case of isononanoic acids having some extent of α-branching, the signal group around 2.3 ppm indicates not only —$CH_2$—COOR but also —CH—COOR— groups, the signal group of the esterified OCH groups of the isosorbide at from 5.3 to 5.5 ppm is utilized as reference. In principle, any commercially available NMR equipment can be used for the NMR spectroscopic studies. Avance 500 equipment from Bruker was used for the present NMR spectroscopy study. The spectra were recorded at a temperature of 303 K with a delay of d1=5 seconds, 32 scans, a 30° pulse and a sweep width of 10 000 Hz, with a 5 mm BBO (broad band observer) probe. The resonance signals are recorded with respect to the chemical shifts of tetramethylsilane (TMS=0 ppm) as internal standard. Comparable results are obtained using the same operating parameters with other commercially available NMR equipment.

The $^1$H NMR spectra obtained for the mixtures of diesters of isosorbide have, in the range from 0.5 ppm as far as the minimum in the lowest value in the range from 0.9 to 1.1 ppm, resonance signals formed via the signals of the hydrogen atoms of the methyl group(s) of the carboxylic acid groups. The signals in the range of chemical shifts from 3.5 to 5.5 ppm can be attributed to the signals of the parent isosorbide structure, there being some extent of overlap of the individual signals from the total of 8 protons (1+1):1:1:(1+1+1):1. Quantification is achieved by determining the area under the respective resonance signals, i.e. the area enclosed by the signal and the base line. Commercially available NMR equipment has devices for integration of signal area. The present NMR spectroscopy study used "xwinnmr", version 3.5 software for integration. The ratio was then calculated of the integral values for the signals in the range from 0.5 as far as the minimum in the lowest value in the range from 0.9 to 1.1 ppm (=I($CH_3$)) and of the signals in the range from 5.0 to 5.3 ppm (=I(OCH)), these being respectively divided by the number of corresponding protons. Since three hydrogen atoms are present per methyl group and each molecule comprises two $C_9$ acid radicals, the intensity of the $CH_3$ group signal has to be divided by 6; since 2 esterified OCH groups of the isosorbide are present per molecule, this signal has to be divided by 2 in order to obtain the number of methyl groups per isononanoyl radical. Since a linear primary nonanoic acid which has only one methyl end group contains no branching and accordingly has to have a degree of branching of 0, the quantity 1 then has to be subtracted from this value.

The degree of branching V can also be calculated from the following equation from the intensity ratio measured:

$$V = \frac{\frac{I_{CH_3}}{6}}{\frac{I_{OCH}}{2}} - 1$$

V=average degree of branching, i.e. number of branching points per $C_9$ acid radical $I(CH_3)$=area integral from 0.5 to about 1.0 ppm, attributed to the methyl hydrogen atoms $I(OCH)$=area integral from 5.0 to 5.3 ppm, for the esterified OCH groups of the isosorbide.

As an alternative, the degree of branching can also be determined by converting the carboxylic acids used for esterification into the methyl esters and then, by analogy with the process described above, determining the intensity of the signals ($I(CH_3)$) belonging to the methyl groups of the alkyl radical in relation to the intensity of the methoxy signal of the ester group ($I(OCH_3)$), and calculating the ratio of these two with respect to one another. An advantage of this method is that it can also be used on ring-substituted diesters. In this procedure, the degree of branching can be determined from the following equation:

$$V = [I(CH_3)/I(OCH_3)] - 1$$

To give the diesters of the formula I, in particular the isosorbide diesters, the widest possible application profile, they should preferably be liquid at room temperature and have minimum viscosity. In the case of phthalic esters, viscosity falls as linearity increases in the nonyl alcohol ($C_9$ alcohol) or nonyl alcohol mixture ($C_9$ alcohol mixture) used. Di-n-nonyl phthalate therefore has the lowest viscosity and is therefore easiest to process. Surprisingly, it has been found that the situation is completely different with diesters of the formula I, in particular with the isosorbide diesters. If isosorbide is esterified with pelargonic acid (n-nonanoic acid), the plasticizer produced is solid at room temperature (Mp from differential scanning calorimetry DSC measurements: 27° C., "onset") and cannot therefore be used by way of example for most plastisol applications without considerable extra cost. Furthermore, the diester of 3,5,5-trimethylhexanoic acid, which is also commercially available, has only very restricted flowability at room temperature (melting point 21.7° C., "onset" in DSC measurement). In contrast, the inventive diesters of the formula I, in particular isosorbide diesters, which are based on at least two different carboxylic acids of the empirical formula $C_8H_{17}COOH$, have good flowability and, as shown in the examples, good performance characteristics. In particular, those diesters of the formula I, in particular isosorbide diesters, which are based on a mixture of carboxylic acids of the empirical formula $C_8H_{17}COOH$ which have been prepared from the dimers of 1- or 2-butene have particularly good suitability.

The composition of the inventive mixtures of diesters of the formula I can vary:

a) The inventive mixture can comprise exclusively diesters all comprising the same bicyclic substructure of formula I, and the individual diester isomers differ only via differently structured carboxylic acid radicals. This type of mixture is therefore composed of diester isomers all of which have the same dianhydrohexitol-derivative parent skeleton. The isomerism consists in the presence of at least two different $C_9$ carboxylic acid radicals, and therefore the individual diester isomers can comprise two respectively identical or different $C_9$ carboxylic acid radicals. If only two different $C_9$ carboxylic acid radicals are present, the mixture therefore comprises at most 4, or in the case of isosorbide diesters at most 3, different diester isomers.

b) The inventive mixture can by way of example comprise at least two diester isomers having different bicyclic substructures of formula I which differ via their configuration. This type of mixture can therefore be composed of diester isomers which have two or more dianhydrohexitol-derivative parent skeletons with different configuration. Again, at least two different $C_9$ carboxylic acid radicals are present.

c) The inventive mixture can by way of example comprise at least two diesters with different molar masses. This type of mixture can be composed of diesters which have two or more dianhydrohexitol-derivative parent skeletons with different molar mass (resulting from substitution of the parent skeleton). Again, at least two $C_9$ carboxylic acid radicals whose constitution differs are present.

d) The inventive mixture can comprise not only diesters of different molar mass but also diester isomers having a different configuration of the bicyclic substructure.

It can be advantageous if the diesters of the formula I present in the inventive mixture are those, and in particular are exclusively those, in which each of the radicals $R^1$ to $R^8$ is H.

A feature of one particularly preferred inventive mixture is that the diesters of the formula I present are exclusively diesters of the formula Ia

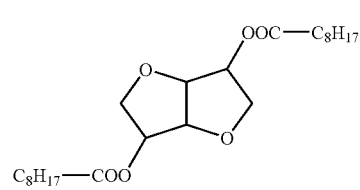

Ia where the chiral C atoms of the underlying bicyclic skeleton can, independently of each other, have R or S configuration. As a function of the relative position of the acid groups, the diesters of the formula Ia can be the diesters of isomannide, or isoidide or of isosorbide. It is particularly preferable that the diesters of the formula I in the mixture are exclusively diesters of isosorbide.

The inventive mixture can either be composed exclusively of the diesters of the formula I or comprise, alongside these, at least one polymer and/or at least one plasticizer which is not a diester of the formula I. The plasticizers can by way of example have been selected from the trialkyl citrates, acylated trialkyl citrates, glycerol esters, glycol dibenzoates, alkyl benzoates, dialkyl adipates, trialkyl trimellitates, dialkyl terephthalates, dialkyl phthalates or the dialkyl esters of 1,2-, 1,3- or 1,4-cyclohexanedicarboxylic acids, the alkyl radicals having from 4 to 13 carbon atoms, preferably 5, 6, 7, 8, 9, 10, 11, 12 or 13 carbon atoms. The plasticizers can also be dianhydrohexitol esters, preferably iso-sorbide diesters, of other carboxylic acids, e.g. n- or isobutyric acid, valeric acid or 2-ethylhexanoic acid. Polymers which can be present in the inventive mixture are polyvinyl chloride (PVC), polyvinyl butyral (PVB) and the polyalkyl methacrylates (PAMA). The polymer polyvinyl chloride (PVC) is particularly preferred.

The ratio by weight of polymer(s) to diester(s) of the formula I in preferred mixtures which comprise diesters of the formula I and polymers is preferably from 30:1 to 1:2.5 and with preference from 20:1 to 1:2.

The molar ratio of plasticizers, in particular of alkyl benzoates, dialkyl adipates, trialkyl citrates, acylated trialkyl citrates, trialkyl trimellitates, glycol dibenzoates, dialkyl terephthalates, dialkyl phthalates, dialkanoyl esters of isosorbide and/or the dialkyl esters of 1,2-, 1,3- or 1,4-cyclohexanedicarboxylic acids, to diester(s) of the formula I in preferred mixtures which comprise diesters of the formula I and plasticizers which are not diesters of the formula I is preferably from 1:10 to 10:1, with preference from 1:6 to 6:1.

There are various ways of preparing the inventive mixtures of diester of the formula I and, respectively, the diesters of the formula I themselves. The mixtures of diesters of the formula I and, respectively, the diesters of the formula I are preferably prepared by the process described below.

A feature of the inventive process for preparation of diesters of the formula I

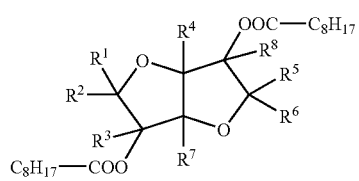

I where $R^1$ to $R^8$=H or alkyl group having from 1 to 6 carbon atoms, $R^1$ to $R^8$ being identical or different, is that a hexahydric alcohol of the formula II

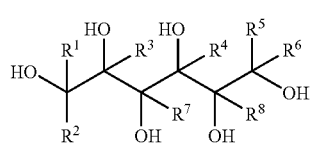

II where the radicals $R^1$ to $R^8$ are as defined in formula I, and/or an anhydro or dianhydro derivative of an alcohol of the formula II is reacted with a mixture which comprises at least two different carboxylic acids of the empirical formula $C_8H_{17}COOH$.

It is preferable to use a carboxylic acid mixture which comprises at least two carboxylic acids of the empirical formula $C_8H_{17}COOH$ with different constitutional formula, the proportion present of any of the carboxylic acids present in the mixture not being more than 95 mol %, preferably at least 90 mol %.

It is preferable that the mixtures of isomeric carboxylic acids of the empirical formula $C_8H_{17}COOH$ used in the inventive process comprise less than 10 mol %, preferably less than 5 mol %, with preference less than 1 mol % and in particular from 0 to 0.5 mol %, with preference less than 0.1 mol %, in particular from 0.0001 to 0.1 mol % and with particular preference less than 0.05 mol %, in particular from 0.01 to 0.05 mol %, of 3,5,5-trimethylhexanoic acid or of other triply substituted carboxylic acids with the empirical formula $C_8H_{17}COOH$, in particular of those having quaternary carbon atoms. The conventional measurement methods familiar to the person skilled in the art can be used to determine the isomer distributions of the isomeric carboxylic acids in the mixtures, examples being NMR spectroscopy, or GC or GC/MS, preferably after conversion to the silyl ester or methyl ester.

In the inventive process, it is particularly preferable to use a mixture of isomeric carboxylic acids of the empirical formula $C_8H_{17}COOH$ which has an average degree of branching of from 0.7 to 2.0, preferably from 1.0 to 1.9, with preference from 1.1 to 1.8 and with particular preference from 1.1 to 1.7. By way of example, the degree of branching of n-nonanoic acid is 0, and the degree of branching of 3,5,5-trimethylhexanoic acid is 3. The degree of branching of the mixture is calculated from the total of the degrees of branching of the individual components multiplied by the respective proportion by weight or molar proportion of the individual component and divided by the total of the proportions of all of the individual components.

In the simplest case, the degree of branching for mixtures can be determined via direct determination of the proportions of the individual components. If this type of determination is not possible, the degree of branching for mixtures of isomeric nonanoic acids can by way of example be determined by means of $^1H$ NMR by analogy with the method described above.

Nonanoic Acid Preparation

In principle, it is possible to use any of the industrial mixtures of carboxylic acids with the empirical formula $C_8H_{17}COOH$ which comprise at least two different constitutional isomers. It is preferable to use those mixtures of isomeric carboxylic acids with the empirical formula $C_8H_{17}COOH$ which lie within the ranges stated above with respect to the proportion of the various isomers, the average degree of branching and/or the content of 3,3,5-trimethylhexanoic acid.

The mixtures of isomeric carboxylic acids with the empirical formula $C_8H_{17}COOH$ (hereinafter called isomeric nonanoic acids) used in the inventive process can by way of example be prepared via hydroformylation of octenes, which in turn can be produced in various ways, and subsequent oxidation.

The raw material used for preparation of the octenes can generally comprise industrial $C_4$ streams, which initially comprise all of the isomeric $C_4$ olefins alongside the saturated butanes and sometimes contaminants such as $C_3$ and $C_5$ olefins and acetylenic compounds. Oligomerization of the olefins present in the $C_4$ streams gives predominantly isomeric octene mixtures, alongside higher oligomers, such as $C_{12}$ and $C_{16}$ olefin mixtures. These octene mixtures can, if appropriate after distillative removal of the $C_{12}$ and $C_{16}$ olefins, be hydroformylated to give the corresponding aldehydes and can then be oxidized to give the carboxylic acid. The composition, i.e. the isomer distribution, of the industrial nonanoic acid mixtures depends on the starting material and on the oligomerization process, oxidation process and hydro-formylation process.

Other octene mixtures that can be used by way of example are those obtained via what is known as the polygas process, which oligomerizes $C_3/C_4$ mixtures on a solid acidic catalyst, preferably on a solid phosphoric acid catalyst (SPA process). This process is described inter alia in the documents U.S. Pat. Nos. 6,284,938, 6,080,903, 6,072,093, 6,025,533, 5,990,367, 5,895,830, 5,856,604, 5,847,252 and 5,081,086. If olefin mixtures obtained exclusively in this way are hydro-formylated, the product generally also includes proportions of octanals and decanals, and the average chain length here can therefore deviate from 9 carbon atoms. The oxidation reaction therefore gives a mixture which comprises isomeric nonanoic acids and which can also comprise isomers of octanoic or decanoic acid.

This has no effect on determination of the degree of branching V according to the abovementioned method.

Octenes from ethylene oligomerization can also be used advantageously.

Particularly preferred mixtures of isomeric nonanoic acids that can be used in the inventive process are those obtainable via hydroformylation of isomeric octenes and subsequent oxidation of the aldehydes obtained and, if appropriate, of alcohols produced, where the mixture of isomeric octenes is obtained by bringing a hydrocarbon mixture which comprises butenes and which comprises a proportion of isobutene which is preferably smaller than 20% by weight, with preference smaller than 10% by weight, with particular preference smaller than 5% by weight, with very particular preference smaller than 3% by weight, particularly preferably smaller than 1% by weight, preferably from 0.01 to 1% by weight and with particular preference from 0.05 to 0.5% by weight, based on the butenes, into contact with an oligomerization catalyst, in particular with a catalyst comprising nickel oxide. Preparation of isomeric octenes via oligomerization of substantially linear butenes on supported nickel catalysts is known by way of example as the OCTOL process, which is described by way of example in EP 0 395 857 or EP 1 029 839. Variants of the OCTOL process utilize for example catalysts comprising Ti or Zr. Alternative variants of this type and in particular the catalysts are described in EP 1 171 413 for example. As described above, the octenes obtained can be isolated by distillation from the higher olefins, i.e. the $C_{12}$, $C_{16}$, $C_{20}$, etc., olefins.

Hydroformylation

The octenes or mixtures of isomeric octenes prepared by way of example as described above are introduced into a hydroformylation reaction. The hydroformylation reaction can take place in the presence of modified or unmodified catalysts composed of cobalt or of rhodium. The hydroformylation reaction preferably takes place in the presence of unmodified cobalt compounds. Suitable hydroformylation processes are disclosed by way of example in EP 0 850 905 and EP 1 172 349. This method generally produces a mixture composed of substantially isomeric nonanals, and possibly of unreacted octenes and of the corresponding mixtures composed of isomeric nonanols and octanes produced via hydrogenation (subsequent reaction).

The hydroformylation reaction can also be carried out in the presence of rhodium catalysts. These hydroformylation processes are well known, for example from EP 0 213 639, EP 1 201, 675, WO 03/16320, WO 03/16321, WO 2005/090276 and from the specifications cited therein. Specific processes for hydroformylation which are likewise suitable for preparation of mixtures of isomeric nonanoic acids that can be used in the inventive process are described by way of example in WO 2004/020380 or DE 103 27 435. The processes described in these publications are carried out in the presence of cyclic carbonic esters.

It can also be advantageous to begin by fractionating the mixture of isomeric octenes, as described in EP 1 172 349, prior to introduction into the hydroformylation reaction. This method can give octene fractions with particularly good suitability for preparation of mixtures of isomeric nonanoic acids that can be used in the inventive process. From the fractions it is then relatively simple to obtain, via mixing of suitable fractions, a mixture of isomeric octenes which is suitable for preparation of mixtures of isomeric nonanoic acids for use in the inventive process.

The reaction mixture from the hydroformylation reaction can optionally be, and is preferably, fractionated, thus concentrating the nonanal fraction destined for the oxidation reaction. Distillative purification is advisable particularly if a relatively high proportion of nonanols is still present in the mixture of nonanals destined for the oxidation reaction.

Hydroformylation of the octene mixtures can be carried out in one or more stages, optionally with isolation of the unreacted octenes after each stage.

Oxidation

Oxidation of the $C_9$ aldehyde or of the two or more isomeric $C_9$ aldehydes present in a mixture, to give the corresponding carboxylic acids, can take place in a manner known per se. Examples of oxidants that can be used are oxygen, air or other oxygen-containing gases. The oxidation reaction can be uncatalysed or catalysed. In the latter case it can be advantageous to use compounds of transition metals, in particular cobalt, as catalysts. Oxidation of the aldehydes can be carried out at atmospheric pressure or at elevated pressure (from 1 to 10 bar, preferably from 1.1 to 5 bar). The reaction temperatures are in the range from 30° C. to 150° C., preferably from 40 to 90° C., particularly preferably from 50 to 80° C. The reaction times can be matched to the oxidation conditions mentioned and can amount to from a few minutes to several hours.

The carboxylic acid(s) can be obtained from the oxidation mixture via distillation at atmospheric pressure or at reduced pressure. If appropriate, the carboxylic acid mixtures can be separated into fractions with different carboxylic acids. Again, this method can then give nonanoic acid fractions which have particular suitability for preparation of the inventive dianhydrohexitol esters, preferably isosorbide diesters of the formula I. This fractionation and subsequent mixing of the fractions with one another or else with other carboxylic acid mixtures in particular makes it possible to combine carboxylic acid mixtures which comprise the abovementioned preferred proportions of certain components or have a certain degree of branching. This simple method can give mixtures of diesters of the formula I which have the desired properties.

However, the inventive process can also use, as mixture, a mixture of isomeric nonanoic acids which is obtainable via mixing of isomerically pure nonanoic acids and/or fractions of a plurality of isomeric nonanoic acids. At least two isomerically pure nonanoic acids are commercially available, namely n-nonanoic acid (pelargonic acid) and 3,5,5-trimethylhexanoic acid CAS number 3302-10-1). There are also commercially available nonanoic acid mixtures or nonanoic acid fractions which do not have the properties preferred for the inventive process. These in essence involve mixtures of multiply branched isononanoic acids with a high proportion (from 93 to 95%) of 3,5,5-trimethyl-hexanoic acid (CAS number 26896-18-4, Celanese). Mixtures of nonanoic acids which on esterification lead to diesters of the formula I with the desired properties can be prepared via simple mixing of these isomerically pure nonanoic acids with other isomerically pure nonanoic acids or with nonanoic acid mixtures. In particular, this simple mixing process can give mixtures of nonanoic acids which comprise the desired proportion of 3,5,5-trimethylhexanol and of other components.

Starting Alcohol

The alcohol component used in the inventive process has been selected from an alcohol of the formula II or a dianhydro or monoanhydro derivative of this alcohol. The alcohol used of the formula II is preferably an alcohol in which the radicals $R^1$ to $R^8$ are respectively H, or a dianhydro or monoanhydro derivative of this alcohol. Particular preference among this group is given to the hexitols sorbitol, mannitol and iditol, sorbitol being very particularly preferred. It is also possible to use mixtures of the abovementioned compounds.

The dianhydro derivative used of an alcohol of the formula II is preferably isosorbide or one of its configurational isomers isomannide or isoidide IIa

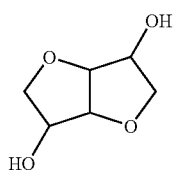

which can be obtained via double dehydration (intra-molecular etherification) starting from the alcohol of the formula II in which all of the radicals $R^1$ to $R^8$ are respectively H (sorbitol, mannitol or iditol), or via single dehydration starting from the corresponding monoanhydro derivative (sorbitan, mannitan or iditan) of the formula IIb

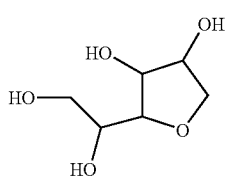

It is particularly preferable that the dianhydro derivative used of an alcohol of the formula II is isosorbide.

Sorbitol in particular is commercially available in quantities of several hundred thousand tonnes annually, and several producers have posted significant isosorbide capacities, and supply of raw material has therefore been ensured, at least in the medium term.

The inventive diesters of the formula I can formally be prepared in various ways, details of which are given below.

Firstly, diester preparation can start from the dianhydro derivative of the alcohol of the formula I and proceed via esterification with a mixture of at least two isomeric nonanoic acids. Esterification of dianhydrohexitols, in particular of isosorbide, with various aliphatic carboxylic acids is the subject of various detailed descriptions in the literature. The dianhydrohexitol is generally reacted with the carboxylic acid in the presence of a catalyst to give the corresponding diester of the dianhydrohexitol.

The reaction preferably takes place with an excess of carboxylic acid (i.e. more than two molar equivalents), preferably with a molar excess of from 10 to 100%, with preference from 20 to 50%. Various processes can be used for removal, from the reaction mixture, of the water formed during the esterification reaction. By way of example, the water can be driven off via an inert gas stream passed through the reaction mixture, or can be removed by means of vacuum. Water can also be removed via azeotropic distillation, either via use of an entrainer, such as toluene, benzene, xylene or cyclohexane, or by using the carboxylic acid itself as entrainer and using the carboxylic acid to replace, to some extent or entirely, the quantity removed by distillation. An overview of the processes described in the literature is found in WO 2006/103338. That reference describes not only the prior art but also a process for preparation of dianhydrohexitol diesters.

Secondly, the inventive diesters of the formula I can be prepared starting from the hexitol of the formula II via a reaction sequence, composed of a double intramolecular elimination of water to give the dianhydro derivative with subsequent or simultaneous esterification, or starting from the monoanhydro derivative of the hexitol of the formula II, and involving single intramolecular elimination of water to give the dianhydro derivative with subsequent or simultaneous esterification. The two individual steps of the reaction (esterification and single or double elimination of water) can be carried out separately or else in the form of what is known as a one-pot reaction. A description of the method is found by way of example in WO 01/83488.

Dehydration (Intramolecular Etherification)

If the monoanhydro derivative of an alcohol of the formula II is used, this is formally converted into the dianhydro derivative in a preceding or simultaneous intramolecular water-elimination reaction. If a hexahydric alcohol of the formula II is used, this is formally converted to the dianhydro derivative or, respectively, monoanhydro derivative in a preceding or simultaneous double or single intramolecular water-elimination reaction, the monoanhydro derivative likewise being converted to the dianhydro derivative in a further intramolecular water-elimination reaction.

In one embodiment of the inventive process, the dehydration reaction (water-elimination reaction) of the alcohol of the formula II or of the corresponding anhydro derivative to give the dianhydro derivative according to formula IIc

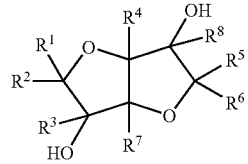

where $R^1$ to $R^8$ are defined as in formula I can be carried out in a separate step prior to the esterification reaction. The reaction mixture thus obtainable, which in essence comprises the dianhydro derivative and monoanhydro derivative of the hexitol with by-products, is then either introduced directly to the esterification process or optionally first worked up, examples of possibilities here being removal of the dehydration catalyst and use of purification steps, such as distillation, crystallization, washing, decolorization, etc., to increase the purity of the dianhydrohexitol needed for the next step of the reaction.

In this embodiment of the inventive process, the dehydration reaction (intramolecular etherification reaction) is preferably carried out at a temperature of from 100 to 200° C., with preference from 110 to 180° C., if the intention is to dehydrate sorbitol or its monoanhydro derivative, and with particular preference at a temperature of from 120 to 150° C., at atmospheric pressure or under a slight vacuum. In this embodiment, the dehydration reaction is preferably carried out in the presence of a catalyst. If the dehydration mixture proceeds directly to further esterification, it is particularly preferable to use a catalyst which is identical with the catalyst used in the esterification reaction. According to WO 01/83488, macroporous acidic ion exchangers are particularly suitable for this purpose.

However, for reasons of kinetics, it can prove advantageous in many cases to delay addition of the mixture of isomeric nonanoic acids to the reaction mixture until most of the alcohol of the formula II has been consumed to give the dianhydro derivative and the amount of monoanhydro derivative still present is small (<10%, measurable by way of GC). Otherwise, the second elimination of water from the monoanhydrohexitol to give the dianhydrohexitol competes with the esterification of the monoanhydro derivative, giving lower yields of diisononanoyl esters of the dianhydro-hexitol. The appropriate times at which the carboxylic acid is then preferably added can readily be determined by way of preliminary experiments. These times depend inter alia on the nature and amount of the catalyst and on the temperature.

In the dehydration reaction, it can be advantageous if water formed during the process is removed via passage of a gas through the reaction mixture, in particular an inert gas. An example of an inert gas that can be used is nitrogen.

However, water formed during the dehydration reaction can also be removed from the reaction mixture via distillation. This distillation is preferably carried out under reduced pressure.

In one preferred embodiment of the inventive process, using an alcohol of the formula II or the monoanhydro derivative of the alcohol, in particular of sorbitol or sorbitan, the dehydration reaction and the esterification reaction are carried out in one operation. In this case, the mixture of isomeric nonanoic acids can be added to the reaction mixture at the very start. In selection of the catalysts for the sequence of dehydration and esterification, care should be taken that these have high selectivity towards the diester of the dianhydro derivative, since otherwise it is possible that (undesirably) high proportions of the mono-, di-, tri- or tetraesters of the monoanhydro derivative of the alcohol of the formula II can be produced. Catalysts with particularly good suitability are generally strong Brønsted acids, such as sulphuric acid, or the abovementioned macroporous acidic ion-exchanger resins. Pure Lewis acids, such as tetrabutyl titanate, are often unsuitable for the dehydration stage.

Esterification

The esterification reaction can be carried out in a known manner, e.g. via reaction of alcohols of the formula II or their monoanhydro or dianhydro derivative with a suitable mixture of isomeric nonanoic acids. The esterification reaction can be autocatalysed or catalysed. The esterification reaction preferably takes place in the presence of a catalyst. In principle, it is possible to use any of the known esterification processes in the inventive process. However, the esterification step preferably takes place by a process in which the water produced in the reaction is removed from the reaction via azeotropic distillation with the carboxylic acid, and the amount of liquid removed via the azeotropic distillation is to some extent or completely supplemented by the mixture of the isomeric nonanoic acids. The amount of liquid hereinafter means the volume of liquid removed from the reaction via azeotropic distillation and mainly composed of water of reaction and of isomeric nonanoic acids. Complete replacement of the amount of liquid removed is preferred. This can take place by way of example via fill-level-controlled feed of a mixture of isomeric nonanoic acids into the reactor.

For technical reasons, complete replacement of the amount of liquid removed can be difficult or impossible. In these cases, the amount of liquid removed is replaced only to some extent, e.g. only the mixture of the isomeric nonanoic acids is replaced, but not the water of reaction removed; however the extent of replacement in every case is more than 90%, preferably from 95 to 98%. It can also be necessary to return, into the reactor, more than the amount of liquid removed by distillation, i.e. not only the amount of acid removed but also the water of reaction is replaced and in addition to this further acid is added. In this embodiment of the esterification reaction, from 110 to 100%, preferably from 105 to 100%, of the amount of liquid removed is replaced by acid.

An advantage of this embodiment of the esterification reaction is that the reaction rate is increased in comparison with known batch processes. The result can be a shortening of cycle time, giving higher space-time yield.

The esterification reaction is preferably carried out in a reaction vessel in which the reaction mixture is intensively mixed with the aid of a stirrer or of a circulating pump. The starting materials and the catalyst can be charged to the reactor simultaneously or in succession. If a starting material is solid at the charging temperature, it is useful to use the liquid starting component as initial charge. Solid starting materials can be fed in the form of powder, granules, crystallized material or melt. In order to shorten charging time, it is advisable to start the heating during the charging process. The catalyst can be introduced in pure form or as solution, preferably dissolved in one of the starting materials, at the start or only after reaction temperature has been reached.

The mixture of isomeric nonanoic acids to be reacted, which also serves as entrainer, can be used in stoichiometric excess. An excess of preferably from 5 to 50%, particularly preferably from 10 to 30%, is used.

With respect to the conduct of the esterification reaction (if it starts from the dianhydro derivative) or the sequence composed of dehydration and esterification (if it starts from the hexahydric alcohol of the formula II or its monoanhydro derivative) reference may be made in particular to EP 1 278 752 (WO 01/83488). The processes described in that reference can be used particularly advantageously for synthesis of the inventive esters of the formula Ia.

The esterification reaction starting from pure dianhydro derivative is preferably carried out on a macroporous acidic ion-exchanger resin as esterification catalyst. The reaction temperatures during the esterification reaction are generally subject to an upper limit given by the thermal stability of these resins. As a function of the degree of crosslinking, these resins can therefore be used at maximum temperatures of from 100 to 190° C. The appropriate information is provided by the producer.

A particular group of acidic ion-exchanger resins preferably used in the inventive process is that of those having sulphonic acid groups. Examples of suitable ion-exchanger resins can be those prepared via sulphonation of phenol/aldehyde condensates or of cooligomers of aromatic vinyl compounds. Examples of aromatic vinyl compounds for preparation of the cooligomers are: styrene, vinyltoluene, vinylnaphthalene, vinylethylbenzene, methylstyrene, vinylchlorobenzene, vinylxylene and divinylbenzene. In particular, the cooligomers produced via reaction of styrene with divinylbenzene are used as precursor for preparation of ion-exchanger resins having sulphonic acid groups.

The properties of these resins, in particular specific surface area, porosity, stability, swelling or shrinkage and exchange capacity, can be varied via the preparation process.

The inventive process can use the ion-exchanger resins in their H form. Strongly acidic macroporous resins of styrene-divinylbenzene type are marketed inter alia with the following trade names: Amberlyst 15, Amberlyst 35, Amberlyst 70.

The pore volume of the ion-exchanger resins preferably used is preferably from 0.3 to 0.9 ml/g, in particular from 0.5 to 0.9 ml/g. The particle size of the resins preferably used is preferably from 0.3 mm to 1.5 mm, in particular from 0.5 mm to 1.25 mm. The particle size distribution can be selected to be relatively narrow or relatively wide. It is particularly preferable to use ion-exchanger resins with very uniform particle size. The capacity of the ion-exchanger resins preferably used, based on the form supplied, is preferably from 0.7 to 2.0 eq/l, in particular from 1.1 to 2.0 eg/l, or preferably from 0.5 to 5.5 mol/kg, in particular from 0.8 to 5.5 mol/kg. (The capacity data in mol/kg are based on the ion-exchanger resin in each case dried to constant weight in a stream of hot nitrogen at, for example, 105° C.)

Numerous other catalysts can also be used, besides the ion-exchanger resins, for preparation of the diesters starting from dianhydrohexitol.

These esterification catalysts can be acids, such as sulphuric acid, methanesulphonic acid or p-toluene-sulphonic acid, or metal-containing catalysts. Examples of metal catalysts whose use is particularly preferred are titanic esters, such as tetraisopropyl ortho-titanate or tetrabutyl orthotitanate, and zirconium esters, such as tetrabutyl zirconate. When compared to the catalysts based on proton acids, the metal catalysts are high-temperature catalysts whose full activity is often not reached until temperatures above 180° C. have been reached.

Catalyst concentration depends on the nature of the catalyst. In the case of the titanium compounds preferably used, this is from 0.005 to 1.0% by weight, based on the reaction mixture, in particular from 0.01 to 0.3% by weight.

The reaction temperatures when using titanium catalysts are from 160° C. to 260° C. The ideal temperatures depend on the starting materials, progress of the reaction and catalyst concentration. They can readily be determined for each particular case via experiments. Higher temperatures increase the reaction rates and favour side reactions, such as formation of coloured by-products. For removal of the water of reaction, it is necessary that the mixture of isomeric nonanoic acids can be removed by distillation from the reaction mixture. The desired temperature or the desired temperature range can be adjusted via the pressure in the reaction vessel. In the case of reaction of isosorbide with the mixture of isomeric nonanoic acids using tetrabutyl titanate as catalyst, a temperature from 180 to 260° C., preferably from 210 to 250° C., has proven to be advantageous.

The amount of liquid to be returned to the reaction can be composed to some extent or completely of isomeric nonanoic acids which are obtained via work-up of the azeotropic distillate. It is also possible to carry out the work-up at a later juncture and to use fresh isomeric nonanoic acids, i.e. isomeric nonanoic acids available from a feed vessel, to replace, completely or to some extent, the amount of liquid removed. In other embodiments of the esterification reaction, the liquid removed is worked up to give the isomeric nonanoic acids.

After the end of the reaction, the reaction mixture, which in essence is composed of full ester (target product) and excess carboxylic acid, comprises not only the catalyst and/or its successor products but also small amounts of dianhydrohexitol monoester. Alongside these, there can also be further by-products present, produced via parallel and/or subsequent reactions, in particular the mono-, di-, tri- and tetraesters of the monoanhydro derivative of the hexahydric alcohol of formula II. The crude product mixtures generally have a yellow to dark brown colour, and, to be suitable for industrial use, therefore require purification, which is sometimes complicated. This purification can also be simplified by using catalyst systems such as those described by way of example in WO06/103338.

For work-up of these crude ester mixtures, most of the excess carboxylic acid mixture is removed by means of vacuum distillation and optional steam distillation, in particular in the temperature range from 120 to 225° C. This is followed by the usual steps for neutralization, purification, decolorization and filtration of the crude product, the conduct of which at various junctures and with varying intensity is a function of the intensity of discoloration or the proportion of water-soluble by-products.

Neutralization of the acidic substances, such as carboxylic acids, or, if appropriate, of the acidic catalysts, can be achieved via addition of basic compounds of the alkali metals and of the alkaline earth metals. These can be used in the form of their carbonates, hydrogencarbonates or hydroxides. The neutralizing agent can be used in solid form or preferably as solution, in particular as aqueous solution. Neutralization is preferably carried out after removal of most of the excess carboxylic acid by distillation.

In most cases it is advisable to wash the neutralized crude product one or more times with water or salt solution, in order to permit removal of water-soluble by-products.

Decolorization of the crude product can firstly be undertaken by adsorption on solids with large surface areas, e.g. activated charcoal or else specific polymer adsorber resins, such as those based on styrene and divinylbenzene. As an alternative, it is possible to use hydrogen peroxide or ozone for decolorization. Preliminary experiments can be used to determine which of the variants are selected for the decolorization process. If appropriate, it is also possible to combine two or more of these methods.

After purification has concluded, the product is dried at an elevated temperature in vacuo and then filtered.

Further details of suitable esterification processes which can be used as esterification step in the inventive process can be found by way of example in EP 1 186 593 and EP 1 300 388.

The inventive mixtures which comprise esters of the formula I or are composed of these can be used in a paint, in an ink or in a coating, in a plastisol, in an adhesive or in a component of an adhesive, in a sealing composition, as a plasticizer in a plastic or in a component of a plastic, as a solvent, as a component of a lubricating oil, as a cooling liquid or a drilling fluid or constituent thereof or as an auxiliary during metalworking. Preferred plastisols here are in particular PVC plastisols or PAMA plastisols. Preferred plastics here are in particular polyvinyl chloride (PVC), polyvinyl butyral (PVB), homo- and copolymers based on ethylene, on propylene, on butadiene, on vinyl acetate, on cellulose acetate, on glycidyl acrylate, on glycidyl methacrylate, on methacrylates, on acrylates, on acrylates having, bonded to the oxygen atom of the ester group, alkyl radicals of branched or unbranched alcohols having from one to ten carbon atoms, or on styrene or on acrylonitrile, and homo- or copolymers of cyclic olefins.

The following plastics may be mentioned by way of example as representatives of the above groups: polyacrylates having identical or different alkyl radicals having from 4 to 8 carbon atoms, bonded to the oxygen atom of the ester group, in particular having the n-butyl, n-hexyl, n-octyl and 2-ethylhexyl radical, polymethacrylate, polymethyl methacrylate, methyl acrylate-butyl acrylate copolymers, methyl methacrylate-butyl methacrylate copolymers, or generally polyalkyl methacrylates (PAMA), ethylene-vinyl acetate copolymers, chlorinated polyethylene, nitrile rubber, acrylonitrile-butadiene-styrene copolymers, ethylene-propylene copolymers, ethylene-propylene-diene copolymers, styrene-acrylonitrile copolymers, acrylonitrile-butadiene rubber, styrene-butadiene elastomers, methyl methacrylate-styrene-butadiene copolymers, cellulose acetate, PVB and PVC. A particularly preferred plastic here is PVC.

The inventive mixtures can moreover be used for modification of plastics mixtures, for example of the mixture of a polyolefin with a polyamide.

Compositions composed of plastic(s), in particular PVC or PAMA, which comprise inventive mixtures which comprise esters of the formula I or are composed of these can by way of example be present in the following products: cases for electrical equipment, such as kitchen machines, computer cases, cases and components of audio and television equipment, pipelines, apparatus, cables, wire sheathing, insulating tapes, interior fitments, vehicle-construction products, furniture-construction products, plastisols, floor coverings, medical items, packaging for food or drink, gaskets, composite or other foils, audio discs, synthetic leather, toys, packaging containers, adhesive-tape foils, clothing, coatings, flock products, printed products, fibres for textiles, coated textiles. Compositions composed of plastic, in particular PVC, which comprise inventive mixtures which comprise esters of the formula I or are composed of these can moreover be used by way of example for production of the following products: pipelines, hoses, cables, wire sheathing, insulating tapes, vehicle-construction products, furniture-construction products, plastisols, profiles, floor coverings, medical items (e.g. blood bags, hoses, infusion bags, etc), toys, packaging for food or drink, gaskets, composite or other foils, discs, synthetic leather, wallpapers, packaging containers, adhesive-tape foils, clothing, coatings, or fibres for textiles, shoes, underbody protection, seam sealing, roof sheeting, modelling compositions or balls.

PVC compositions or plastisols which comprise PVC and comprise inventive mixtures which comprise esters of the formula I or are composed of these preferably comprise from 5 to 250 parts by weight, with preference from 10 to 200 parts by weight and with particular preference from 20 to 100 parts by weight, of the inventive mixtures per 100 parts by weight of PVC.

EXAMPLE 1

Synthesis of Isononanoic Acid a) Preparation of $C_9$ Aldehydes Based on Dibutene The starting material used for preparation of $C_9$ aldehydes (isononanals) via hydroformylation of $C_8$ olefins comprised a $C_8$ olefin mixture (dibutene) from the Octol process of OXENO Olefinchemie GmbH. The experimental procedure selected is set out below.

2000 g of dibutene were hydroformylated for 3 hours in the presence of a cobalt catalyst at 175° C. and a synthesis gas pressure of 280 bar in a 5 l high-pressure autoclave with stirrer and electrical heating. The catalyst was prepared by using synthesis gas to treat 640 g of an aqueous cobalt acetate solution with 1.0% by weight of cobalt at 170° C. and 28 MPa, for 6 hours. After cooling and depressurization, the carbonylcobalt compounds formed were transferred to the organic phase via extraction with the 2000 g of di-n-butene and this phase was separated from the aqueous phase. The concentration of the catalyst in the dibutene was 0.02% by weight, based on the dibutene and calculated as cobalt metal. The hydroformylation mixture was then freed from cobalt at 80° C. via treatment with 1000 g of 5% strength aqueous acetic acid in the presence of air, which was passed into the mixture by way of a frit during 30 minutes at through-put of 30 l/h. The hydroformylation mixture freed form cobalt was then separated from the aqueous phase.

The process was carried out four times under the same reaction conditions. The hydroformylation mixtures freed from cobalt were combined. 9450 g of mixture were obtained. The crude product obtained has the following composition in % by weight by gas-chromatographic analysis (GC analysis): 19.8% of $C_8$ hydrocarbons, 57.6% of $C_9$ aldehydes, 18.3% of $C_9$ alcohols, 2.7% of $C_9$ alcohol formates and 1.6% of residue.

The crude product obtained was freed from the unreacted $C_8$ hydrocarbons (low boilers) in a downstream batch distillation process. The following typical composition of the bottom fraction in % by weight was determined by GC analysis: 73.2% of $C_9$ aldehydes, 21.5% of $C_9$ alcohols, 3.1% of $C_9$ alcohol formates and 2.0% of high boilers and 0.2% of $C_8$ hydrocarbons.

The bottom fraction which comprised the useful $C_9$ aldehydes product was then used for preparation of the $C_9$ carboxylic acids.

b) Preparation of $C_9$ Acids Via Oxidation of $C_9$ Aldehydes

The $C_9$ acids were prepared via liquid-phase oxidation of the $C_9$ aldehydes in a heatable 6 l jacketed stirred tank. The starting material used comprised the hydro-formylation product from Example 1a with about 73% by weight of $C_9$ aldehydes.

3500 g of liquid starting material was used as initial charge in the reactor for a reaction batch. The reaction gas used comprised a nitrogen-oxygen mixture, which was distributed uniformly into the liquid by way of a frit in the lower part of the reactor.

A constant stream of nitrogen at 30 Nl/h and a stream of oxygen controlled as a function of consumption via the reaction by way of on-line measurement of oxygen content in the exhaust gas were metered into the reactor. A constant stream of nitrogen at 330 Nl/h was metered into the gas space of the reactor in the upper part of the reactor. Maximum oxygen content permitted in the exhaust gas was 6% by volume. Oxidation of the $C_9$ aldehydes was carried out at a reaction temperature of 55° C. and at a pressure of 0.12 MPa. Progress of the oxidation reaction was determined via regular sampling followed by GC analysis.

Under the reaction conditions selected, a crude product whose composition has been listed in the second column in Table 1 was obtained after the experiment had run for 20 hours. The product obtained from the oxidation reaction was then worked up by batch distillation. For the distillation process, a laboratory packed column (Sulzer DX packing) with 5 l still pot was used. Table 1 lists the composition of the product prior to and after the distillation process.

TABLE 1

| | Product composition | |
| --- | --- | --- |
| Component | Crude product oxidation % by weight | Product after distillation in % by weight |
| $C_8$ hydrocarbons | 0.96 | 0.03 |
| $C_9$ aldehydes (isononanals) | 5.20 | 0.13 |
| Esters (isononyl formates) | 2.96 | 0.02 |
| $C_9$ alcohols (isononanols) | 16.68 | 0.24 |
| $C_9$ acids (isononanoic acids) | 71.33 | 99.36 |
| High boilers | 2.87 | 0.23 |

As can be seen in Table 1, a $C_9$ carboxylic acid mixture of high purity was obtained for the reaction described below.

EXAMPLE 2

Esterification of Isononanoic Acid from Example 1 with Isosorbide (Inventive)

365 g (2.5 mol) of isosorbide (Cerestar) were heated to 230° C., with stirring and nitrogen introduced by bubbling by way of an immersion tube (6 l/h) with 1027 g (6.5 mol) of isononanoic acid of Example 1 and 0.91 g of tetrabutyl orthotitanate (0.25% by weight, based on isosorbide, DuPont, Tyzor TnBT), in a 2 liter multinecked flask with stirrer, water separator, dropping funnel, internal thermometer and immersion tube. Application of a slight vacuum at this temperature ensured that the water of reaction could be discharged completely by way of the water separator. Progress of the reaction was followed by way of GC analysis. After a total of about 8 hours, the reaction had ended and the water separator was replaced by a distillation bridge, permitting removal of the excess isononanoic acid at a temperature of from 200 to 230° C. During this process, the pressure was also reduced successively as far as about 3 hPa. The mixture was then cooled to 80° C. and neutralized with 50 ml of 10% strength sodium hydroxide solution. The crude ester was then washed three times in a separating funnel with in each case 300 ml of 5% strength NaCl solution, and the aqueous phase was in each case removed and discarded. 1% by weight of activated charcoal was then admixed with the mixture, which was dried for one hour in the stirred flask at 125° C. and a pressure of 5 hPa, and filtered after cooling to 100° C. Because the product had an intense colour, the mixture in the stirred flask was again decolorized at 90° C. with 2% by weight of $H_2O_2$ (35% strength, Merck), and then again neutralized (40 ml of 10% strength NaOH), and then again washed twice, dried and filtered. Since the colour was still unsatisfactory, the sequence composed of $H_2O_2$ decolorization, neutralization, washing, drying and filtration as described above was repeated a further two times. The Hazen/APHA colour number of the isosorbide diisononanoate (IsDIN) product thus obtained was 62. Purity, determined by way of GC analysis, was 99% (ester A). The degree of branching of the side chain, determined by way of NMR, was 1.3.

EXAMPLE 3

Esterification of 2-ethylhexanoic Acid with Isosorbide (Comparative Example)

292 g (2 mol) of isosorbide (Cerestar) were heated to 240° C., with stirring and nitrogen introduced by bubbling by way of an immersion tube (6 l/h) with 730 g (5 mol) of 2-ethylhexanoic acid (European Oxo) and 1.46 g of tetrabutyl orthotitanate (0.5% by weight, based on isosorbide, DuPont, Tyzor TnBT), in a 2 liter multinecked flask with stirrer, water separator, dropping funnel, internal thermometer and immersion tube. Application of a slight vacuum at this temperature ensured that the water of reaction could be discharged completely by way of the water separator. Progress of the reaction was followed by way of GC analysis. After a total of about 8 hours, the reaction had ended and the water separator was replaced by a distillation bridge, permitting removal of the excess 2-ethylhexanoic acid at a temperature of 180° C., and at a pressure down to a minimum of 5 hPa. The residue was then decolorized with 2.5% by weight of $H_2O_2$ solution (35% strength, Merck) at from 80 to 90° C., and then, as in Example 2, neutralized with NaOH solution, and then washed and dried. For a further improvement in colour, the mixture was then stirred again with the same amount of $H_2O_2$, then dried at 120° C., and then washed a further two times with 5% strength NaCl solution, and then again dried at 120° C., stirred at this temperature for a further hour with 2% of activated charcoal, and then filtered. The purity of the di-2-ethylhexanoyl-isosorbide ester (IsDEH, ester B) thus obtained was about 99% (GC) and its Hazen colour number was 50, the latter measured by a method based on DIN EN ISO 6271 with LICO 400 colour measurement equipment from Hach-Lange.

EXAMPLE 4

Esterification of 3,5,5-trimethylhexanoic Acid with Isosorbide (Comparative Example)

The di-3,5,5-trimethylhexyl ester of isosorbide was also prepared by a procedure analogous to the synthesis starting from the isononanoic acid of Example 1. The starting material used comprised commercially available 3,5,5-trimethylhexanoic acid ("isononanoic acid", European Oxo).

After various purification steps (see Examples 2 and 3), the purity of the isosorbide di-3,5,5-tri-methylhexanoate ester (IsD355TMH) thus prepared was 98.2% and its Hazen colour number was 68 (see Example 3 for method). The melting point of this ester, measured by DSC (onset), was 21.7° C. It is termed ester C below.

EXAMPLE 5

Esterification of Pelargonic Acid (n-nonanoic Acid) with Isosorbide (Comparative Example)

876 g (6 mol) of isosorbide (Cerestar) were heated to 220° C., with stirring and nitrogen introduced by bubbling by way of an immersion tube (6 l/h) with 2370 g (15 mol) of pelargonic acid (Fluka) and 2.19 g of tetrabutyl orthotitanate (0.25% by weight, based on isosorbide, DuPont, Tyzor TnBT), in a 4 liter multi-necked flask with stirrer, water separator, dropping funnel, internal thermometer and immersion tube. Application of a slight vacuum at this temperature ensured that the water of reaction could be discharged completely by way of the water separator. Progress of the reaction was followed by way of GC analysis. After a total of about 8.5 hours, the reaction had ended and the water separator was replaced by a distillation bridge, by way of which most of the excess pelargonic acid could be removed by distillation at a temperature of 180° C. and at a pressure successively lowered as far as 2 hPa. This was followed by a steam distillation at 180° C. and drying in the presence of activated charcoal (1% by weight). The mixture was then neutralized by analogy with Example 2, washed twice with 250 ml of 5% strength NaCl solution and dried after another steam distillation in vacuo, and then filtered. For further decolorization, it was then stirred with 2% of $H_2O_2$ at a temperature of from 80 to 120° C., and then again neutralized, and washed a further two times and dried after a final steam distillation at 140° C. in vacuo after addition of 1% of activated charcoal, and the mixture was then filtered. The Hazen/APHA colour number of the resultant isosorbide dipelargonate ester (IsDnN) was then 38 (see Example 3 for method) and its purity determined by means of GC was 99%.

The ester solidified on cooling to room temperature, and DSC (Differential Scanning Calorimetry) determination of melting point gave a value of 27° C.

The fact that this ester (ester D) is a solid at room temperature practically excludes its use as sole plasticizer for plastisols, since the paste-like consistency needed for processing (spreading, dipping, spraying, rotomoulding) would be difficult to achieve via addition of further auxiliaries. This ester was therefore not used for further studies.

EXAMPLE 6

Preparation of Isosorbide Esters Based on Mixtures of Pelargonic Acid and 3,5,5-trimethylhexanoic Acid The fact that the esters prepared in Examples 4 and 5 have melting points in the region of ambient temperature makes them appear unsuitable for plastisol processing. Mixing of the two acids and subsequent esterification should enable the tendency toward crystallization to be reduced. To this end, mixtures of pelargonic acid and 3,5,5-trimethylhexanoic acid were prepared according to Table 2, and these were esterified by the processes described above. The table lists not only the molar proportions of the acids in the reaction mixture but also the contents, obtained by means of GC, of isosorbide diesters and their melting points, together with the appropriate values for the esters from Examples 4 and 5.

The melting points were determined by means of DSC, and for this in each case the rise in the melting signal (known as "onset") was utilized. In the case of a plurality of melting points (various phases, e.g. in the case of ester F) the highest melting point was reported, since the first crystallization processes begin below this temperature. All of the esters also have a glass transition temperature, which indicates the presence of fractions having some degree of amorphic character.

TABLE 2

| Example No. | Proportion of pelargonic acid in mixture in mol % | Proportion of 3,5,5-trimethyl-hexanoic acid in mixture in mol % | Purity in % | Melting point of isosorbide esters |
|---|---|---|---|---|
| D | 100 | 0 | 99 | 27° C. |
| E | 95 | 5 | 98.8 | 26.3° C. |
| F | 60 | 40 | 98.4 | 4° C. |
| G | 5 | 95 | 98 | 22.4° C. |
| C | 0 | 100 | 98.2 | 21.7° C. |

Use of the esters in which one of the acids is present at a proportion of 95 mol % or above in plastisol processes at room temperature is impossible or possible only at disproportionately high cost and inconvenience, because of their high melting points. The inventive ester F can in turn be processed without difficulty at room temperature.

EXAMPLE 7

Plastisol Preparation

The starting weights used of the components for the various plastisols are found in the table below.

TABLE 3

| Formulations according to example (all data in phr (=parts by weight per 100 parts by weight of PVC)) | | | |
|---|---|---|---|
| Plastisol formulation | 1 | 2 | 3 |
| Vestolit B 7021 (Vestolit (GmbH) | 100 | 100 | 100 |
| Vestinol 9 (DINP of OXENO Olefinchemie) | 50 | | |
| Diisononanoylisosorbide ester (IsDIN of Example 2, inventive) | | 50 | |
| Di-2-ethylhexanoylisoborbide ester (IsDEH of Example 3, Comparative Example) | | | 50 |
| Epoxidized soya bean oil (Drapex 39, Crompton) | 3 | 3 | 3 |
| Mark CZ 140 (Crompton) | 1.5 | 1.5 | 1.5 |

The temperature of the plasticizers was controlled to 25° C. prior to addition. The liquid constituents were weighed out first into a PE beaker and were followed by the pulverulent constituents. The mixture was stirred manually with a paste spatula in such a way that no unwetted powder remained. The mixing beaker was then clamped into the clamping apparatus of a dissolver stirrer. Before the stirrer was immersed in the mixture, the rotation rate was adjusted to 1800 revolutions per minute. After the stirrer had been switched on, stirring was continued until the temperature on the digital display of the heat sensor reached 30.0° C. This ensured that homogenization of the plastisol was achieved with defined energy input. The temperature of the plastisol was then immediately controlled to 25.0° C.

EXAMPLE 8

Gelling Curve Measurement

The gelling behaviour of the plastisols was studied in a Bohlin CVO oscillation viscometer (PP20 measurement system), operated using shear stress control.

The following parameters were set:
Mode: Temperature gradient
Start temperature: 25° C.
End temperature: 180° C.
Heating/cooling rate: 2° C./min
Temperature after measurement: 25° C.
Oscillation frequency: 2 Hz
Delay time: 1 s
Waiting time: 15 s
Continuous oscillation: on
Automatic shear stress preset: on
Initial shear stress: 0.3 Pa
Specified deformation: 0.002
Gap width: 0.5 mm Test Method:

A spatula was used to apply a droplet of the plastisol formulation to be tested, free from air bubbles, to the lower plate of the measurement system. Care was taken here to provide the possibility for some plastisol to expand out from the measurement system uniformly (not more than about 6 mm around the periphery) after the measurement system had been closed together. The protective covering, which also serves for thermal insulation, was then applied, and the test was started.

The variable known as complex viscosity of the plastisols was plotted as a function of temperature in FIG. 1. The inventive plastisol 2 (IsDIN) is shown by the continuous line with filled-in circles, plastisol 1 (Vestinol 9) by the broken line with diamonds and the comparative example using IsDEH as plasticizer by the dotted line with triangles. Onset of gelling is generally discernible in a sudden sharp rise in complex viscosity. The earlier the onset of this viscosity rise, the better the gelling capability of the system, generally.

Result: Gelling of the plastisol with the inventive ester IsDIN is comparable with that based on the corresponding phthalate DINP and also only slightly slower than for IsDEH.

EXAMPLE 9

Plastisol Viscosity Measurement

The viscosities of the plastisols prepared in Example 7 were measured as follows by a method based on DIN 53 019 by a Physica DSR 4000 rheometer (Paar-Physica), controlled by way of the associated US 200 software.

The plastisol was again stirred with a spatula in the storage container and tested using measurement system Z3 (DIN 25 mm) in accordance with the operating instructions. The test proceeded automatically at 25° C. by way of the abovementioned software. The following conditions will apply:

Pre-shear of 100 $s^{-1}$ for a period of 60 s, without recording any test values A downward gradient, starting at 200 $s^{-1}$ and extending downward as far as 0.1 $s^{-1}$, divided into a logarithmic series with 30 steps with in each case a measurement point duration of 5 s.

The test data were automatically processed by the software after the test. Viscosity was shown as a function of shear rate. The tests were carried out after each of 2 h, 4 h, 24 h and 28 days. The paste was stored at 25° C. between these junctures.

Table 4 below lists by way of example for the shear rate of 100 $s^{-1}$ in each case the corresponding viscosity values obtained after the stated storage times.

TABLE 4

Shear rate 100 $s^{-1}$ (viscosity data in Pa * s)

| Plastisol formulation | Plasticizer used | 2 h | 24 h | 7 d | 28 d | Total rise from 2 h after 28 days in % |
|---|---|---|---|---|---|---|
| 1 | DINP (Vestinol 9) | 3.44 | 3.88 | 4.1 | 5.12 | 49% |
| 2 | IsDIN of Example 2 | 6.34 | 6.63 | 7.32 | 7.58 | 20% |
| 3 | IsDEH of Example 3 | 6.42 | 6.62 | 7.4 | 8.09 | 26% |

The viscosity of the inventive plastisol 2 is comparable with that of the comparative example with IsDEH as plasticizer. The inventive plastisol exhibits the best storage stability.

EXAMPLE 10

Foil Production

To produce the test specimens, foils of thickness 1 mm were first produced for each formulation in Table 3. For this, high-gloss release paper (Sappi, Italy) was first cut to a size of 30*44 cm and was then placed in the clamping frame of the LTSV spreader equipment for a Mathis oven. The clamping frame was then placed on the guide frame, the Mathis oven (LTF type) was set to 200° C., and once this temperature had been reached the frame was preheated for 15 seconds. The doctor was then placed in the clamping apparatus and the doctor gap was adjusted by way of preliminary experiments in such a way that the thickness of the foil after conclusion of gelling was 1 mm (±0.05 mm). An adhesive strip was applied to the front edge of the paper in order to intercept excess paste. The paste was then applied in front of the doctor and was spread (speed about 6 m/min) by drawing the guide frame with the doctor over the clamped release paper. The doctor was then removed and the adhesive strip with the excess paste was taken away. The melt roll was then lowered and the clamping frame was run into the oven. After gelling (2 minutes at 200° C.), the frame was run back out of the oven and, after cooling, the foil was peeled from the paper.

EXAMPLE 11

Measurement of Volatility from Foil by Method Based on DIN 53 407

The foils produced in Example 10 of thickness about 1 mm were in each case used to stamp out three discs with diameter 50 mm, these being first stored for 24 h in standard conditions of temperature and humidity (23° C./50% relative humidity) and then weighed. Using a method based on DIN 53 407, the discs are then in each case heated at 80° C. in a heating cabinet for 24 hours (Method A, direct contact with activated charcoal, particle size 2.5 mm). The discs are then in turn removed from the heating cabinet, cooled for 24 hours under standard conditions of temperature and humidity, and again weighed before they are again stored in the heating cabinet. The test was ended after a storage period of 7*24 hours. Table 5 lists the test values obtained:

TABLE 5

Volatility measurement results

| Plastisol formulation | Plasticizer used | 1 d | 2 d | 3 d | 4 d | 5 d | 6 d | 7 d |
|---|---|---|---|---|---|---|---|---|
| 1 | Vestinol 9 (DINP) | 0.7 | 1.1 | 1.53 | 1.86 | 2.19 | 2.4 | 2.74 |
| 2 | IsDIN of Example 2 | 0.86 | 1.24 | 1.57 | 1.91 | 2.27 | 2.47 | 2.79 |
| 3 | IsDEH of Example 3 | 1.34 | 2.47 | 3.8 | 4.85 | 5.9 | 6.69 | 7.74 |

Result:
The volatility of the foils produced from the inventive esters corresponds to that of those produced from the corresponding phthalate DINP and is markedly lower than that of the comparative product IsDEH and of IsD355TMH.

EXAMPLE 12

Measurement of Glass Transition Temperatures of Foils

Sections of length 60 mm, width 80 mm and thickness 1 mm were stamped out from the foils produced in Example 10 and in each case stiffness G' and loss modulus G" were determined on these to DIN EN ISO 6721 (Part 2) at temperatures from −100° C. to +100° C. and frequency of 1 $s^{-1}$ using a MYRENNE ATM III torsion pendulum.

The glass transition temperature $T_G$ can be determined from the maximum of G", and is a measure of flexibility at low temperatures.

Table 6 lists the glass transition temperatures for the test specimens:

TABLE 6

Glass transition temperatures of foils

| Foils composed of plastisol formulation No. | Plasticizer used | Glass transition temperature $T_G$ |
|---|---|---|
| 1 | Vestinol 9 (DINP) | −31° C. |
| 2 | IsDIN of Example 2 | −16° C. |
| 3 | IsDEH of Example 3 | −11° C. |

The glass transition temperature of the foils produced from the inventive diisononanoyl esters is markedly lower than that of the foil produced from IsDEH (comparative example), although poorer than for the corresponding phthalate DINP.

SUMMARY

It can therefore be stated that the inventive diisononanoylisosorbide esters (IsDIN) exhibit good plasticizer properties and have performance characteristics superior to those of the isosorbide esters prepared from 2-ethylhexanoic acid (IsDEH, Example 3), 3,5,5-trimethylhexanoic acid (IsD355TMH, Example 4) and pelargonic acid (IsDnN, Example 5).

The invention claimed is:

1. A mixture, comprising:
at least two different diesters of formula I:

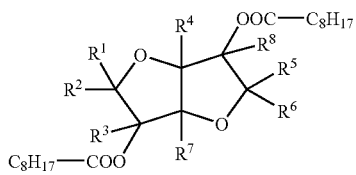

wherein each of $R^1$ to $R^8$ is independently H or an alkyl group having from 1 to 6 carbon atoms, and
$C_8H_{17}COO$ groups of at least two of the diesters of formula I are nonidentical isomers.
2. The mixture of claim 1, wherein
a proportion of $C_8H_{17}COO$ groups of any one structure is not more than 95 mol % of all $C_8H_{17}COO$ groups in the diesters.
3. The mixture of claim 1,
wherein less than 10 mol % of $C_8H_{17}$ groups in the diesters are 3,5,5-trimethylpentyl groups.
4. The mixture of claim 1,
wherein $C_8H_{17}COO$ groups of the diesters have a degree of branching of from 0.7 to 2.0.
5. The mixture of claim 1,
wherein $C_8H_{17}COO$ groups of the diesters have a degree of branching of from 1.2 to 1.9.
6. The mixture of claim 1,
wherein each of $R^1$ to $R^8$ is H.
7. The mixture of claim 1,
wherein the diesters comprise at least two different bicyclic substructures of formula I, which differ in configuration.
8. The mixture of claim 1,
wherein the diesters comprise at least two diesters with different molar masses.
9. The mixture of claim 1,
wherein the diesters comprise at least two diesters of different molar masses, and
the diesters comprise at least two different bicyclic substructures of different configurations.
10. The mixture of claim 1,
wherein the diesters in the mixture all comprise identical bicyclic substructures of formula I, and
individual diester isomers differ only via differently structured $C_8H_{17}COO$ groups.
11. The mixture of claim 1,
wherein the two different diesters of formula I are diesters of formula Ia:

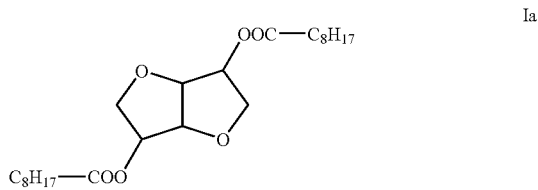

wherein chiral C atoms of the bicyclic skeleton can, independently of each other, have R or S configuration.
12. The mixture of claim 10,
wherein the two different diesters are diesters of isosorbide.
13. The mixture of claim 1, further comprising: a polymer, another plasticizer that is not a diester of the formula I, or both.
14. The mixture of claim 13, comprising a polymer,
wherein a ratio by weight of polymer to diesters of formula I is from 30:1 to 1:2.5.
15. The mixture of claim 13, comprising another plasticizer that is not a diester of the formula I,
wherein a molar ratio of the other plasticizer to the diesters of formula I is from 1:10 to 10:1.
16. The mixture of claim 13, comprising a polymer,
wherein the polymer is PVC.
17. A process for preparing a dianhydrohexitol diester mixture, the process comprising:
reacting a hexahydric alcohol of formula II:

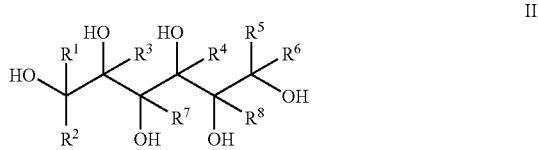

an anhydro or dianhydro derivative of an alcohol of formula II, or a mixture thereof with a carboxylic acid mixture comprising at least two different carboxylic acids of formula $C_8H_{17}COOH$, to obtain the dianhydrohexitol diester mixture,
wherein the dianhydrohexitol diester mixture comprises at least two different diesters of formula I:

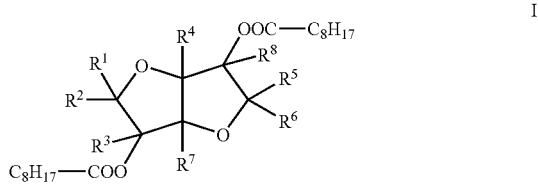

each of $R^1$ to $R^8$ is independently H or an alkyl group having from 1 to 6 carbon atoms, and $C_8H_{17}COO$ groups of at least two of the diesters of formula I are nonidentical isomers.

18. The process of claim 17,
wherein the carboxylic acid mixture has an average degree of branching from 0.7 to 2.0.

19. The process of claim 17,
wherein the reacting comprises:
dehydrating the alcohol of formula II or a monoanhydro derivative of an alcohol of formula II, to obtain an alcohol dehydration product, then
separately esterifying the alcohol dehydration product with the carboxylic acid mixture, to obtain the dianhydrohexitol diester mixture.

20. The process of claim 17,
wherein the reacting comprises:
dehydrating and esterifying an alcohol of formula II or a monoanhydro derivative of an alcohol of formula II in one operation.

21. The process of claim 17,
wherein the reacting comprises dehydrating at a temperature of from 100 to 180° C.

22. The process of claim 17,
wherein the reacting comprises:
dehydrating to obtain a dehydration product in the presence of a catalyst, and
esterifying in the presence of the catalyst.

23. The process of claim 17,
wherein the reacting comprises esterifying on an acidic ion-exchanger resin.

24. The process of claim 17, further comprising:
passing an inert gas through a reaction mixture of the reacting, thereby removing water.

25. The process of claim 17, further comprising:
distilling a reaction mixture of the reacting, thereby removing water.

26. The process of claim 17,
wherein the reacting comprises esterifying, and
wherein a temperature of esterifying is from 120 to 260° C.

27. The process of claim 17,
wherein the reacting comprises dehydrating and subsequently, separately esterifying, and
wherein a temperature of esterifying is from 130 to 180° C.

28. A paint, an ink, a coating, a plastisol, an adhesive, a component of an adhesive, a sealing composition, a plasticizer in a plastic, a plasticizer in a component of a plastic, a solvent, a component of a lubricating oil, or an auxiliary during metalworking, comprising the mixture of claim 1.

29. A PVC plastic or component thereof, comprising the mixture of claim 1.

30. A PVC plastisol, comprising the mixture of claim 1.

31. A PVC composition, comprising:
PVC and
the mixture of claim 1,
wherein the composition has a content of from 5 to 250 parts by weight of the mixture of claim 1 per 100 parts by weight of PVC.

32. A plastisol, comprising:
PVC and
the mixture of claim 1,
wherein the composition has a content of from 5 to 250 parts by weight of the mixture of claim 1 per 100 parts by weight of PVC.

* * * * *